United States Patent [19]

Stevens

[11] Patent Number: 4,889,117

[45] Date of Patent: Dec. 26, 1989

[54] DISPOSABLE LANCET

[76] Inventor: Peter A. Stevens, 1492 Landings Lake Dr., Sarasota, Fla. 34231

[21] Appl. No.: 312,951

[22] Filed: Feb. 17, 1989

[51] Int. Cl.$^4$ .............................................. A61B 17/34
[52] U.S. Cl. .................................. 606/181; 128/329 R
[58] Field of Search .................... 128/314, 315, 329 R, 128/763, 770

[56] References Cited

U.S. PATENT DOCUMENTS

| | | | |
|---|---|---|---|
| 4,078,552 | 3/1978 | Chen et al. | 128/314 X |
| 4,469,110 | 9/1984 | Slama | 128/314 X |
| 4,577,630 | 3/1986 | Nitzsche et al. | 128/314 |
| 4,616,649 | 10/1986 | Burns | 128/314 |
| 4,712,548 | 12/1987 | Enstrom | 128/314 |

Primary Examiner—Michael H. Thaler
Attorney, Agent, or Firm—Charles J. Prescott

[57] ABSTRACT

A disposable lancet for piercing a person's finger skin sufficiently to let a small quantity of blood. The lancet includes a long, slender, rigid shank having a hypodermic needle-style piercing tip at one end and slidably mounted within a generally coextensive support tube over substantially its entire length. A cap is connected to the other end of the shank which, when in contact with one end of the support tube, is structured to allow the piercing tip to extend beyond the other end of the support tube a predetermined distance sufficient for piercing the skin. The shank has a stored position wherein the piercing tip is retracted fully within the support tube. Single-use features are also disclosed.

7 Claims, 1 Drawing Sheet

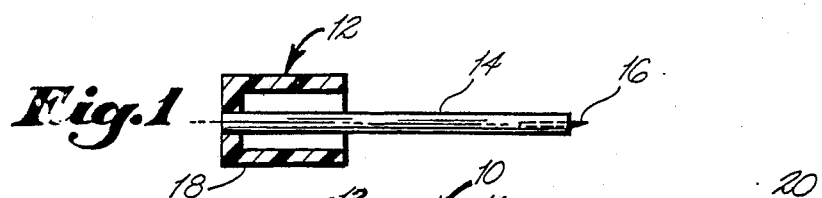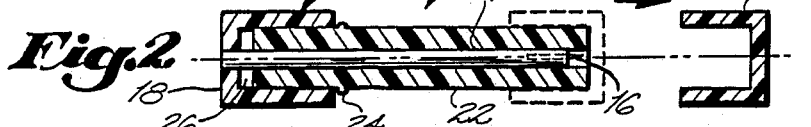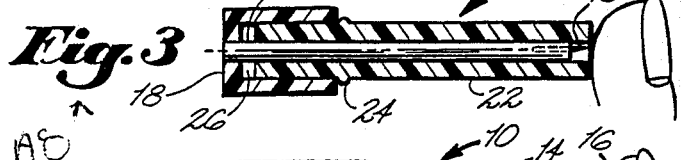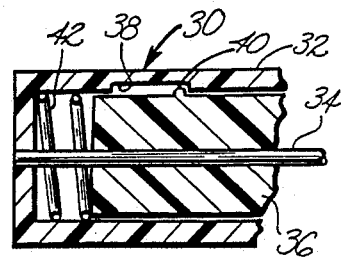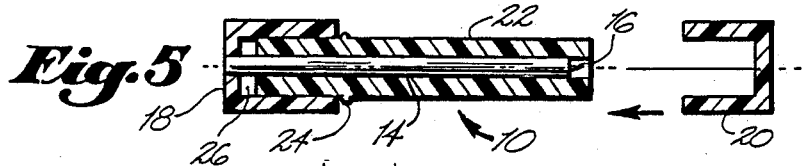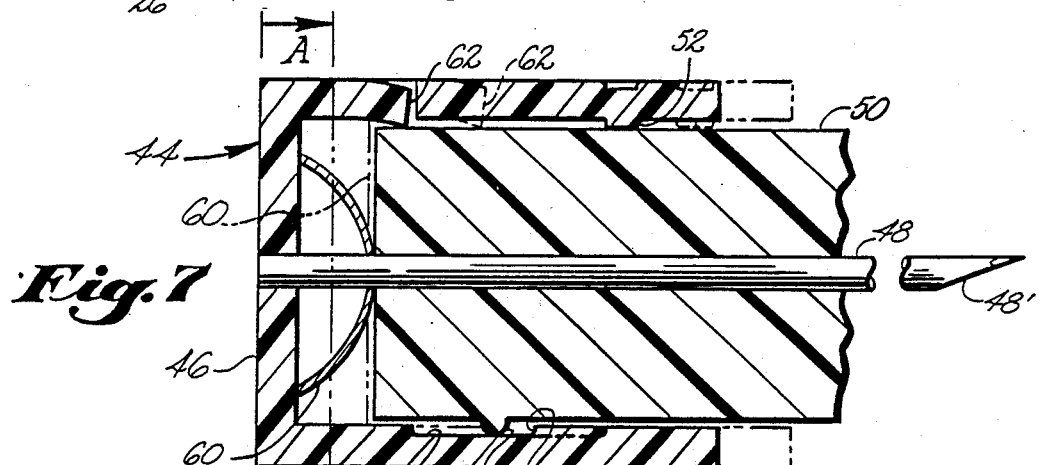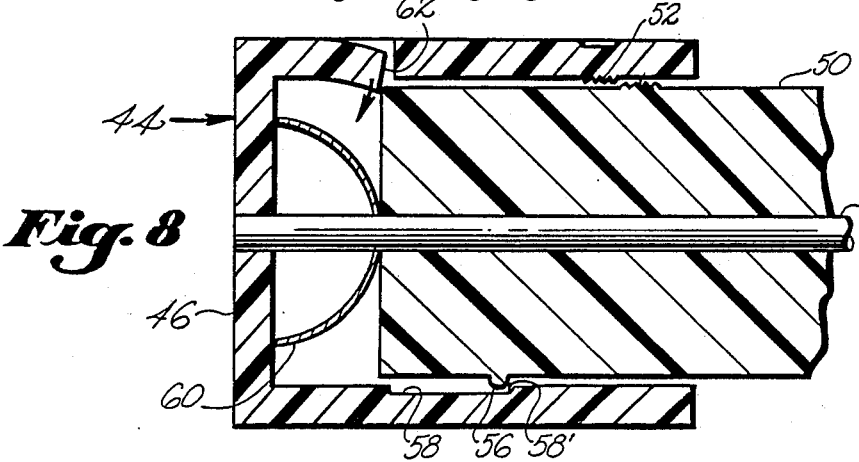

DISPOSABLE LANCET

BACKGROUND OF THE INVENTION

This invention relates generally to blood lancets, and more particularly to a lancet for finger piercing with improved structural safety features and functional benefits.

The letting of small quantities of blood for certain testing purposes has become part of an extremely important diagnostic technique. However, with increasing utilization of this technique, not only in institutional settings, but also most recently in home use wherein diabetics and certain other patients periodically let and test their own blood samples, improved devices have been developed and marketed to facilitate this procedure.

As a substitute for early techniques of simply manually pricking the finger with a pointed needle, various systems have been invented and marketed which facilitate this function. These systems typically include a reusable carrier mechanism and a disposable lancet which is installed and used in conjunction therewith.

Two lancets for use in conjunction with these carrying devices are known to applicant under the trademarks MONOLET by Sherwood Medical Industries, the other under the trademark MICROFINE by Beckton Dickinson and Company.

One such lancet carrier device is disclosed in U.S. Pat. No. 4,230,118 which is directed to a device marketed by Owen Mumford, Ltd. under the trademark AUTOLET which forces a spring-loaded pivoted arm carrying a replaceable disposable lancet through a replaceable apertured plate which is pressed against the patient's finger. Controlled penetration and pressure are achieved to effect a quick and relatively painless puncturing of the skin of the finger. Another such unpatented device is now marketed under the trademark AUTOLANCE by Becton Dickinson and Company. This device, used in conjunction with the disposable MICRO-FINE lancet, is similar in function to the '118 patent except that the device is longitudinal in nature and does not include a replaceable pad for pressing against the skin. Sherwood also produces a carrier under the trademark MONOJECTOR which is similar to the AUTOLANCE device.

All of the above prior art devices, however require that a lancet surrounded in molded plastic be installed into and removed from the carrier each time so as to reduce the possibility of transmitting blood diseases from one patient to another. However, because of the nature of replacing lancets, the exposed piercing tip may accidentally puncture the operator's finger during the replacement procedure. Further, these lancets are installed and removed with the carrier in its cocked position. This risk is particularly acute to the medical practitioner who inadvertently pierces his own finger after use, thus encountering the risk of contamination of his own blood supply if the patient carries contaminated blood. There appears to be an additional risk associated with the AUTOLANCE device in that the portion of the reusable mechanism which presses against the patient's finger and comes in contact with blood let is not replaceable and must somehow be sterilized after each use.

The present invention avoids all of the above limitations while providing an economical, disposable and, if desired, simple lancet which is useable only one time.

The invention eliminates or substantially reduces risk of inadvertent piercing of a medical technician's fingers because the piercing tip is always concealed except during momentary use. Further, the entire device is disposable rather than being replaceable within a larger reusable mechanism during which time needle exposure would otherwise serve as a danger to the technician.

BRIEF SUMMARY OF THE INVENTION

This invention is directed to a disposable lancet for piercing a person's finger skin sufficiently to let a small quantity of blood. The lancet includes a long, slender, rigid shank having a hypodermic needle-style piercing tip at one end and slidably mounted within a generally coextensive support tube over substantially its entire length. A cap is connected to the other end of the shank which, when in contact with one end of the support tube, is structured to allow the piercing tip to extend beyond the other end of the support tube a predetermined distance sufficient for piercing the skin. The shank has a stored position wherein the piercing tip is retracted fully within the support tube. Single-use features are also disclosed.

It is therefore an object of this invention to provide an economical, disposable lancet which minimizes or eliminates risk of accidental skin puncture.

It is another object of this invention to provide an economical to manufacture disposable lancet.

It is another object of this invention to provide a disposable lancet which eliminates risk of cross contamination of blood between patients.

It is another object of this invention to provide a disposable lancet which may only be used one time.

In accordance with these and other objects which will become apparent hereinafter, the instant invention will now be described with reference to the accompanying drawings in which:

BRIEF DESCRIPTION OF THE DRAWINGS

FIG. 1 is a side elevation section view of one embodiment of the shank, piercing tip and cap of the invention.

FIG. 2 is a side elevation section view of FIG. 1 including the protective support tube in place and showing the removal of the protective end cover.

FIG. 3 is a side elevation section view of FIG. 2 showing the invention ready for use.

FIG. 4 is a side elevation section view of FIG. 2 during momentary use in piercing the skin of the finger.

FIG. 5 is a side elevation section view of FIG. 2 after use showing replacement of the protective end cover for disposal.

FIG. 6 is an enlarged partial side elevation section view of another embodiment of the invention.

FIG. 7 is an enlarged partial side elevation section view of the preferred embodiment of the invention.

FIG. 8 is a view of FIG. 7 after one time use.

DETAILED DESCRIPTION OF THE INVENTION

Referring now to the drawings, and particularly to FIGS. 1 to 5, one embodiment of the invention, in perhaps its most simplest form, is shown generally at numeral 10. This embodiment 10 includes a lancet shown generally at numeral 12 having an elongated rigid, slender tubular shaft or shank 14 with a hypodermic needle-style piercing tip 16 disposed from its distal end as best seen in FIG. 1. Connected at the other end of shank 14 is a cap 18 formed of molded plastic and generally of a cup-shaped configuration.

This lancet 12 is structured such that shank 14 will slidably engage within protective support tube 22 over substantially the entire length of shank 14. Cap 18 is sized and structured so as to slidably engage over the outer surface over the corresponding end of protective tube 22.

The relative lengths between shank 14 and protective tube 22 are such that, when cap 18 is disposed a certain distance 26 from the corresponding end of protective tube 22, piercing tip 16 is fully within the protective tube 22 as best seen in FIGS. 2 and 3. However, when cap 18 is moved against the corresponding end of protective tube 22 as shown in FIG. 4, the piercing tip 16 extends longitudinally outward from the other end of protective tube 22 to effect finger skin piercing.

At least one bump or protrusion 24 is provided positioned so as to serve as a detent to inhibit cap 18 from being moved so as to contact the corresponding end of protective tube 22 except when the device 10 is to be used to pierce the skin of the finger. Then, sufficient force may be exerted against cap 18 in the direction of the arrow shown in FIG. 4 so as to overcome the slight interference posed by bumps 24 wherein cap 18 will override this obstruction so as to extend piercing tip 16 beyond the other end of protective tube 22 for use.

A molded cover 20 is also provided which frictionally engages over the other end of molded plastic protective tube 22. Cover 20 is provided to be heat sealed over support tube 22, as is cap 18, so as to insure sterility of piercing tip 16 prior to use. Cover 20 also is provided to be reinstalled as shown in FIG. 5 after the device 10 is used so as to prevent blood from coming in contact with other persons and to help insure that no further contact is made with piercing tip 16.

Note that, although shank 14 is here shown as a slender metal thin-wall tube into which piercing tip 16 is forcedly inserted, nonetheless the entire shank 14 and piercing tip 16 may be fabricated alternately of a single length of rigid wire. When fabricated in two parts, the shank 14 also provides an additional shoulder to further insure controlled piercing depth of piercing tip 16.

Although the invention is described in its simplest form in FIGS. 1 to 5, the entire device 10 may be incorporated into a reuseable carrying device such as in the shape of a typical mechanical ball point pen wherein cover 18 is structured to cooperatively interengage with the well-known ball point pen mechanism which is then used to forceably urge cap 18 in the direction of the arrow in FIG. 4 so as to expose piercing tip 16 for use. Additionally, well-known means for momentary inertia or spring biasing may be provided (not shown).

Although the distal end of support tube 22 is applied against the fingertip skin and is exposed to blood let as a result of the piercing action, because the entire device 10 is intended for only one time use and to be disposed of thereafter, there is no risk of cross contamination between patients.

In addition to providing bumps 24 as previously described, cap 18 and cover 20 are also preferably heat sealed or spot welded as will be described and shown with respect to FIGS. 7 and 8 herebelow so as to ensure sterility from time of manufacture until time of actual use.

Referring now to FIG. 6, an alternate embodiment of the lancet is shown generally at numeral 30 and includes a plastic molded cap 32, again generally cup-shaped, which slideably engages over support tube 36 as previously described, this cap 32 is heat sealed to plastic support shaft 36 at assembly to help insure sterility. In this embodiment 30, a solid surgical steel shank 34 is utilized rigidly connected into cap 32 as shown. The opposite end of shank 34 includes a formed hypodermic-type piercing tip positioned with respect to the distal end of support tube 36 as previously described.

In this embodiment of lancet 30, a compression return spring 42 is provided which automatically withdraws the piercing tip end (not shown) of shank 34 within the support tube 36 after use. Bump 40 slideably engages within cavity 38 so as to limit the relative longitudinal travel between cap 32 and support tube 36, and this controls the distance of extension of the piercing tip beyond the end of support tube 36.

Referring lastly to FIGS. 7 and 8, the lancet shown generally at 44 is provided to offer the limited one time use feature. In this embodiment 44, again a solid shank 48 is utilized having a piercing tip 48' at its distal end as shown in FIG. 7. The shank 48 is rigidly connected into cup-shaped plastic molded cap 46 as previously described. Plastic support tube 50 serves to allow shank 48 to translate longitudinally therewithin.

In this embodiment 44, a spring steel formed washer 60 is provided to afford the automatic return feature in lieu of a conventional compression coil spring shown in FIG. 6. Spring washer 60 compressively flattens as shown in phantom in FIG. 7 into a thinner overall dimension than coil spring 42 in FIG. 6 and is preferred.

Bump 56 translates longitudinally within cavity 58 so as to suitably limit the longitudinal travel of shank 48 and cap 46 relative to support tube 50 so as to both control the extending of piercing tip 48' beyond the distal end of support tube 50 and to limit the distance of return of cap 46 away from the corresponding end of support tube 50 so that the entire assembly remains intact after use for disposal.

In this embodiment 44, a spot weld or heat seal is provided at 52 so as to insure sterility of the piercing tip 48' prior to use in conjunction with a molded cover 20 at the opposite end of support tube 50 as previously described with respect to FIGS. 2 to 5. However, the spot weld 52 also longitudinally secures cap 46 with respect to support shaft 50 so that inwardly biased tang 62 is pressed against the side of support shaft 50 on assembly. However, at use, cap 46 is displaced against the corresponding end of support shaft 50, moving a distance equal to arrow A. Spring washer 60 flattens to the orientation shown in phantom while piercing tip 48 is extended to accomplish its blood-letting purposes. Thereafter, when axial force is released from cap 46, it is allowed to travel in the opposite direction away from the corresponding end of support tube 50 a distance somewhat further than dimension A as controlled by the position of the end 58' of cavity 58 as best seen in FIG. 8. When allowed to return this additional distance after use, inwardly biased tang 62 then moves in the direction of the arrow as shown in FIG. 8 so as to impinge upon the corresponding end of support tube 50 and to remain there by its spring biasing configuration.

This structural arrangement shown in FIG. 8 is achieved after a one-time cycling of the device 44. In this configuration, then the longitudinal positional relationship between support tube 50 and cap 46/shank 48/piercing tip/48' is fixed by the interaction of tang 62 against the corresponding end of support tube 50 and bump 56 against the end 58' of cavity 58. Further relative axial movement between the components is impossible short of damaging the components. Thus, inadvertent reuse of the device is virtually impossible.

While the instant invention has been shown and described herein in what is conceived to be the most practical and preferred embodiment, it is recognized that departures may be made therefrom within the scope of the invention, which is therefore not to be limited to the details disclosed herein, but is to be accorded the full scope of the claims so as to embrace any and all equivalent apparatus and articles.

What is claimed is:

1. A disposable lancet for piercing a person's finger skin sufficiently deep to let a small quantity of blood comprising:
    a rigid, slender, elongated shank having a hypodermic needle-style piercing tip connected and longitudinally disposed at one end for piercing the skin;
    a protective support tube having a first and second end and generally coextensive with, and surrounding said shank such that said shank is slidable longitudinally in said support tube;
    a cap connected to the outer end of said shank and at least partially surrounding said first end of said protective tube such that, when said cap is pressed against said first end of said support tube by movement longitudinally in one direction, said piercing tip extends outwardly beyond said second end of said support tube a predetermined distance to an in-use position sufficient for piercing the skin;
    said cap movable longitudinally in the opposite direction away from said first end of said support tube into a first stored position wherein said piercing tip is withdrawn into, and protectively concealed by, said second end of said support tube;
    said cap having an inner generally cylindrical surface and a recess disposed in said inner cylindrical surface of said cap; and
    a projection on said support tube disposed within said recess such that longitudinal travel of said cap with respect to said support tube is limited by the length of said recess.

2. A disposable lancet as set forth in claim 1, further comprising:
    a protective end cover generally cup-shaped and structured to releasably engage over said support tube second end to protect said piercing tip.

3. A disposable lancet as set forth in claim 1, further comprising:
    a detent stop formed on said support tube structured to cooperatively act with said cap to inhibit inadvertent movement of said shank which extends said piercing tip outward beyond said second end of said support tube.

4. A disposable lancet as set forth in claim 1, further comprising:
    a compression biasing member disposed between said cap in said support tube structured to maintain said piercing tip in its first stored position except when overcome by an external force against said cap.

5. A disposable lancet as set forth in claim 4, further comprising:
    a spot weld between the interior of said cap and said support tube to retain said piercing tip in its said first stored position until being overcome by an external force against said cap.

6. A disposable lancet as set forth in claim 5, further comprising:
    a moveable spring-biased stop connected to said cap and structured to bias against the side of, and to allow, said support tube to move freely with respect to said cap until said spot weld has been disengaged and said piercing tip has been moved to a second stored position wherein said cap is moved further away from said first end of said support tube than when in said first stored position;
    said spring-biased stop positively engaging against said first end of said support tube thus preventing said cap from moving further toward said first end of said support tube.

7. A disposable lancet as set forth in claim 1, wherein: said shank is a hollow, thin-walled tube; said piercing tip is rigidly connected within one end of said shank.

* * * * *